(12) United States Patent
Kim et al.

(10) Patent No.: US 12,391,941 B2
(45) Date of Patent: Aug. 19, 2025

(54) EXTENDED SINGLE GUIDE RNA AND USE THEREOF

(71) Applicant: INSTITUTE FOR BASIC SCIENCE, Daejeon (KR)

(72) Inventors: Jin-Soo Kim, Seoul (KR); Ka Yeong Lim, Seoul (KR); Beum-Chang Kang, Busan (KR); Seuk Min Ryu, Seoul (KR)

(73) Assignee: INSTITUTE FOR BASIC SCIENCE, Daejeon (KR)

( * ) Notice: Subject to any disclaimer, the term of this patent is extended or adjusted under 35 U.S.C. 154(b) by 621 days.

(21) Appl. No.: 16/964,277

(22) PCT Filed: Jan. 23, 2019

(86) PCT No.: PCT/KR2019/000962
§ 371 (c)(1),
(2) Date: Jul. 23, 2020

(87) PCT Pub. No.: WO2019/147014
PCT Pub. Date: Aug. 1, 2019

(65) Prior Publication Data
US 2021/0032621 A1 Feb. 4, 2021

(30) Foreign Application Priority Data
Jan. 23, 2018 (KR) .................. 10-2018-0008492

(51) Int. Cl.
| C12N 15/11 | (2006.01) |
| C12N 9/22 | (2006.01) |
| C12N 15/113 | (2010.01) |
| C12N 15/90 | (2006.01) |

(52) U.S. Cl.
CPC ............... *C12N 15/11* (2013.01); *C12N 9/22* (2013.01); *C12N 15/907* (2013.01); *C12N 2310/20* (2017.05)

(58) Field of Classification Search
CPC .... C12N 15/102; C12N 15/11; C12N 15/113; C12N 15/907; C12N 9/22; C12N 2310/20
See application file for complete search history.

(56) References Cited

U.S. PATENT DOCUMENTS

| 10,519,454 B2 * | 12/2019 | Kim ................ C12N 9/16 |
| 11,192,929 B2 * | 12/2021 | Harris .............. C12N 15/1082 |
| 2010/0076057 A1 | 3/2010 | Sontheimer et al. |

FOREIGN PATENT DOCUMENTS

| CN | 101611154 | 12/2009 |
| CN | 105899657 | 8/2016 |
| CN | 105934516 | 9/2016 |
| CN | 106834341 | 6/2017 |
| EP | 3009511 | 4/2016 |
| JP | 2016-500003 | 1/2016 |
| JP | 2017-520243 | 7/2017 |
| KR | 10-2016-0133380 | 11/2016 |
| KR | 10-2017-0068400 | 6/2017 |
| WO | 2015-133554 | 9/2015 |
| WO | 2016/134081 | 8/2016 |
| WO | 2017/070632 | 4/2017 |
| WO | 2017-183724 | 10/2017 |

OTHER PUBLICATIONS

Nishida K. et al., Targeted nucleotide editing using hybrid prokaryotic and vertebrate adaptive immune systems. Science. Sep. 16, 2016;353(6305):aaf8729. doi: 10.1126/science.aaf8729. Epub Aug. 4, 2016 (Year: 2016).*
Zhang et al., Different Effects of sgRNA Length on CRISPR-mediated Gene Knockout Efficiency, Scientific Reports, 2016, 6, 1-10. ( Jun. 24, 2016) (Year: 2016).*
Zhang XH et al. Off-target Effects in CRISPR/Cas9-mediated Genome Engineering. Mol Ther Nucleic Acids. Nov. 17, 2015;4(11): e264. doi: 10.1038/mtna.2015.37. PMID: 26575098; PMCID: PMC4877446. (Year: 2015).*
Bin Li et al., "Engineering CRISPR-Cpf1 crRNAs and mRNAs to maximize genome editing efficiency", Nat Biomed Eng. 1(5), May 10, 2017. doi:10.1038/s41551-017-0066.
F Ann Ran et al., "Genome engineering using the CRISPR-Cas9 system", Nat Protoc, 8(11): 2281-2308. Oct. 24, 2013. doi:10.1038/nprot.2013.143.
Je Wook Woo et al., "DNANA-free genome editing in plants with preassembled CRISCRISCRISCRISPR-Cas9 ribonucleoproteins", nature biotechnology, vol. 33, No. 11, Oct. 19, 2015. doi:10.1038/nbt.3389.
Jian-Ping Zhang et al, "Different effects of sgRNA length on CRISPR-mediated gene knockout efficiency", Scientific Reports, vol. 6, No. 1, Jun. 1, 2016.
Yuan Zong et al., "Precise base editing in rice, wheat and maize with a Cas9-cytidine deaminase fusion", Nature Biotechnology, vol. 35, No. 5, pp. 438-440, Feb. 27, 2017.
EPO, Supplementary European Search Report of EP patent application No. 19743145.5, Sep. 17, 2021.
JPO, Office Action of patent application No. 2020-561562, Sep. 17, 2021.
Satomi Banno et al., "Deaminase-mediated multiplex genome editing in *Escherichia coli*", Nature Microbiology vol. 3, pp. 423-429 (2018), Feb. 5, 2018, https://doi.org/10.1038/s41564-017-0102-6.
Tomoko Kato-Inui et al., "Clustered regularly interspaced short palindromic repeats (CRISPR)/CRISPR-associated protein 9 with improved proof-reading enhances homology-directed repair", Nucleic Acids Research, vol. 46, Issue 9, May 18, 2018, pp. 4677-4688, https://doi.org/10.1093/nar/gky264.
Seuk-Min Ryu et al., "Adenine base editing in mouse embryos and an adult mouse model of Duchenne muscular dystrophy", Nature Biotechnology vol. 36, pp. 536-539, Apr. 27, 2018, https://doi.org/10.1038/nbt.4148.

(Continued)

*Primary Examiner* — Maria G Leavitt
*Assistant Examiner* — Vyoma Shubham Tiwari
(74) *Attorney, Agent, or Firm* — LEX IP MEISTER, PLLC

(57) ABSTRACT

The present disclosure relates to: an extended guide RNA and a composition for base editing, comprising the same; and a method for base editing and a method for producing genetically modified animals or plants, both methods using the composition for base editing.

3 Claims, 18 Drawing Sheets
Specification includes a Sequence Listing.

(56) References Cited

OTHER PUBLICATIONS

JPO, Office Action of JP 2020-561562 dated Apr. 7, 2022.
SIPO, Office Action & Search Report of CN 201980014548.2, dated Mar. 3, 2023.
Daesik Kim et al., "Digenome-seq: genome-wide profiling of CRIScrisPR-Cas9 off-target effects in human cells", Nature Methods, vol. 12 No. 3, pp. 237-243, Feb. 9, 2015.
SIPO, Office Action of CN 201980014548.2 dated Dec. 27, 2023.
SIPO, Search Report of CN 201980014548.2 dated Dec. 26, 2023.

* cited by examiner

WT AAGGAAACTGGAACACAAAGCATAGACTGCGGG SEQ ID NO:2

GX19
AAGGAAACTGGAACGCAAAGCATAGACTGCGGG SEQ ID NO:3
AAGGAAACTGGAACGCGAAGCATAGACTGCGGG SEQ ID NO:4
AAGGAAACTGGAACGCAAGGCATAGACTGCGGG SEQ ID NO:5
AAGGAAACTGGAACGCAGAGCATAGACTGCGGG SEQ ID NO:6
************ *   ****************

GX20
AAGGAAACTGGAACGCGAAGCATAGACTGCGGG SEQ ID NO:7
AAGGAAACTGGAACGCAAAGCATAGACTGCGGG SEQ ID NO:8
AAGGAAACTGGAGCGCAAAGCATAGACTGCGGG SEQ ID NO:9
AAGGAAACTGGAGCGCGAAGCATAGACTGCGGG SEQ ID NO:10
*********** * * *****************

```
      WT CCACGTTCACCTTGCCCCACAGGGCAGTAACGG SEQ ID NO:12
         CCACGTTCACCTTGTTTTACAGGGCAGTAACGG SEQ ID NO:13
   gX19  CCACGTTCACCTTGCTTTACAGGGCAGTAACGG SEQ ID NO:14
         CCACGTTCACCTTGCCTTACAGGGCAGTAACGG SEQ ID NO:15
         *************   ***************

CCACGTTCACCTTGTTTTACAGGGCAGTAACGG SEQ ID NO:16
   gX22  CCACGTTCACCTTGCTTTACAGGGCAGTAACGG SEQ ID NO:17
         CCACGTTTATTTTGTTTTACAGGGCAGTAACGG SEQ ID NO:18
         *******  *  ***  ***************
```

Fig. 5b b

Target sgRNA — PAM

*B. napus* AID2-gX19 treated:
5'- CAGGTCCCTCGCCGGATGATCGGT -3'
Gln Val Pro Arg Arg Met Ile Gly   SEQ ID NO:30

5'- CAGGTCCCTCGCtGGATGATCGGT -3'  1.56%
Gln Val Pro Arg * Met Ile Gly   SEQ ID NO:31

5'- CAGGTttCTCGCtGGATGATCGGT -3'  0.68%
Gln Val * Arg * Met Ile Gly   SEQ ID NO:32

5'- CAGGTtCCTCGCtGGATGATCGGT -3'  0.39%
Gln Val Pro Arg * Met Ile Gly   SEQ ID NO:33

171    173           178

Target sgRNA — PAM

*B. napus* AID2-gX20 treated:
5'- CAGGTCCCTCGCCGGATGATCGGT -3'
Gln Val Pro Arg Arg Met Ile Gly   SEQ ID NO:34

5'- CAGGTCCCTCGCtGGATGATCGGT -3'  2.77%
Gln Val Pro Arg * Met Ile Gly   SEQ ID NO:35

5'- tAGGTCCCTCGCCGGATGATCGGT -3'  1.05%
* Val Pro Arg Arg Met Ile Gly   SEQ ID NO:36

5'- tAGGTCtCTCGCCGGATGATCGGT -3'  0.62%
* Val * Arg Arg Met Ile Gly   SEQ ID NO:37

| | Target sgRNA | PAM | | |
|---|---|---|---|---|
| | 5'- CCAGGTCCCCGGCGCATGATTGG -3' | | | SEQ ID NO:39 |

Glycine max AID2-gX10 treated:

5'- CCAGGTttCCCGGCGCATGATTGG -3'  0.40%  SEQ ID NO:40
5'- CCAGGTCCCCtGGCGCATGATTGG -3'  0.40%  SEQ ID NO:41
5'- CCAGGTtttCtGGCGCATGATTGG -3'  0.29%  SEQ ID NO:42

| | Target sgRNA | PAM | | |
|---|---|---|---|---|
| | 5'- CCAGGTCCCCGGCGCATGATTGG -3' | | | SEQ ID NO:43 |

Glycine max AID2-gX20 treated:

5'- CCAGGTCCCCtGGCGCATGATTGG -3'  2.11%  SEQ ID NO:44
5'- CtAGGTtttCtGGCGCATGATTGG -3'  0.87%  SEQ ID NO:45
5'- CCAGGTtCCCCGGCGCATGATTGG -3'  0.11%  SEQ ID NO:46

Fig. 6b

```
         400 401 422 423 424 425 426
         His Asn Arg Asp Ser Tyr Met       SEQ ID NO:48
         CCATAACAGAGACTCTTACA              Sub (%)
                                                              SEQ ID NO:49
         CCATGGCAGAGACTCTTACATGG    45.2 (N421G)              SEQ ID NO:50
Pup #1   CCGTGACAGAGACTCTTACATGG    25.5 (H420R, N421D)       SEQ ID NO:51
         CCATGACAGAGACTCTTACATGG    22.1 (N421D)              SEQ ID NO:52

CCATGACAGAGACTCTTACATGG    36.4 (N421D)              SEQ ID NO:53
Pup #2   CCATGGCAGAGACTCTTACATGG    35.9 (N421G)              SEQ ID NO:54
         CCGTGGCAGAGACTCTTACATGG    11.4 (H420R, N421G)       SEQ ID NO:55

CCATGGGGAGACTCTTACATGG     40.0 (N421G, R422G)       SEQ ID NO:56
Pup #3   CCGTGACAGAGACTCTTACATGG    27.7 (H420R, N421D)       SEQ ID NO:57
         CCGTGGCAGAGACTCTTACATGG    19.4 (H420R, N421G)       SEQ ID NO:58
         CCATGGCAGAGACTCTTACATGG    4.8  (N421G)              SEQ ID NO:59
```

EXTENDED SINGLE GUIDE RNA AND USE THEREOF

TECHNICAL FIELD

The present disclosure relates to an extended guide RNA, a composition for base editing containing the same, a method for base editing using the composition for base editing and a method for producing genetically modified animals or plants using the composition for base editing.

BACKGROUND ART

Gene-editing technology starts with the immune system, wherein a fragment of a bacteriophage is remembered in the form of DNA through infection with the bacteriophage and then the corresponding DNA is removed by cutting with Cas9 (CRISPR associated protein 9: RNA-guided DNA endonuclease), which is a nuclease acting as gene scissors when secondary infection occurs. This has developed into a gene-editing technology in which, when guide RNA (gRNA) recognizes a specific nucleotide, the Cas9 protein can cut the corresponding site to conduct editing (Ran F. A. et al., *Nat. Protoc.*, 8:2281-2308, 2013, Woo J. W. et al., *Nat. Biotechnol.*, 33: 1162-1164, 2015).

A gene editor for base editing, formed by modifying conventional CRISPR-Cas9 gene scissors, is a technology that has recently attracted attention because it can change specific bases without cutting both strands of DNA. The gene editor for base editing binds to a target site via sgRNA having a sequence complementary to the target DNA and then changes cytosine (C) to uracil (U) or adenine (A) to hypoxanthine (I) using a deaminase capable of acting on single-stranded DNA exposed to the opposite side. The resulting bases are changed to thymine (T) and guanine (G) during DNA repair and replication, and as a result, specific DNA bases can be edited from cytosine (C) to thymine (T) and from adenine (A) to guanine (G), respectively. At this time, the base-editing range in which the base editor operates is known to be located at positions 13 to 17 in the direction of the protospacer from the protospacer adjacent motif (PAM), and efficiency outside the range is very low (FIG. 1A).

Accordingly, in order to overcome the problems described above, the present inventors have found that, when modifying the form and length of the sgRNA, which define the target position of the gene editor for base editing, the range of operation of the gene editor for base editing can be further extended. Based on this finding, the present disclosure has been completed.

DISCLOSURE

Technical Problem

It is one object of the present disclosure to provide an extended guide RNA that can further extend a range of operation of a gene editor for base editing.

It is another object of the present disclosure to provide a composition for base editing including a deaminase, a target-specific nuclease and an extended guide RNA, the composition for base editing capable of further extending the range of operation of a gene editor for base editing.

It is another object of the present disclosure to provide a base-editing method using the composition for base editing.

It is another object of the present disclosure to provide a method for producing a genetically modified animal or plant using the composition for base editing.

Technical Solution

In accordance with one aspect of the present disclosure, the above and other objects can be accomplished by the provision of an extended guide RNA for base editing hybridizable with a target sequence, the extended guide RNA further including 1 to 3 guanines (G) and 1 to 10 nucleotides at the 5' end.

In accordance with another aspect of the present disclosure, provided is a composition for base editing including (i) a deaminase or a gene encoding the same, (ii) an RNA-guided engineered nuclease or a gene encoding the same, and (iii) an extended guide RNA hybridizable with a target sequence or a gene encoding the same, wherein the extended guide RNA further includes 1 to 3 guanines (G) and 1 to 10 nucleotides at the 5' end.

In accordance with another aspect of the present disclosure, provided is a method for base editing including introducing the composition for base editing into cells.

In accordance with another aspect of the present disclosure, provided is a method for producing a mutant adult of a mammal other than a human, or an eukaryotic plant including (a) introducing the composition for base editing into a mammalian embryo or a eukaryotic plant embryo and (b) growing the embryo to obtain an adult.

DESCRIPTION OF DRAWINGS

FIG. 2 shows the change in the base-editing window depending on the length of the sgRNA based on each activity measured by deep-sequencing in the HEK293T cell line, more particularly, FIG. 2C shows the most frequently observed mutation allele, wherein the portion in which the mutation was introduced in the WT sequence is expressed in red.

FIG. 3 shows the change in the base-editing window when using sgRNA further including 1 or 2 additional mismatching G, based on based on each activity measured by deep-sequencing in the HEK293T cell line, more particularly.

FIG. 4 shows the change in the base-editing window depending on the length of the sgRNA at four different sites, based on each activity measured by deep sequencing in the HEK293T cell line, more particularly.

FIG. 5 shows the change in the base-editing window depending on the type of sgRNA in rapeseed and soybean, based on activity measured by deep sequencing, more particularly, FIG. 5B shows the change of alleles introduced with mutations occurring most frequently according to the sgRNA type, wherein it was found that a TAG stop codon was produced only when gX20 sgRNA was used, FIG. 5D shows the change of alleles introduced with mutations occurring most frequently according to the sgRNA type wherein it was found that a TAG stop codon was produced only when gX20 sgRNA was used.

FIG. 6 shows the change in the base-editing window depending on the type of sgRNA in mice, more particularly, FIG. 6B shows the result of analyzing pups obtained by performing microinjection into embryos using ABE 7.10 mRNA in combination with GX21 sgRNA, wherein three pups with desired H420R mutations were obtained.

BEST MODE

Unless defined otherwise, all technical and scientific terms used herein have the same meanings as appreciated by those skilled in the field to which the present disclosure pertains. In general, the nomenclature used herein is well-known in the art and is ordinarily used.

The present disclosure suggests a technique for further expanding the range of operation of the gene editor for base editing by modifying the form and length of sgRNA that define the target position of the gene editor for base editing (FIG. 1B).

Figure 1:
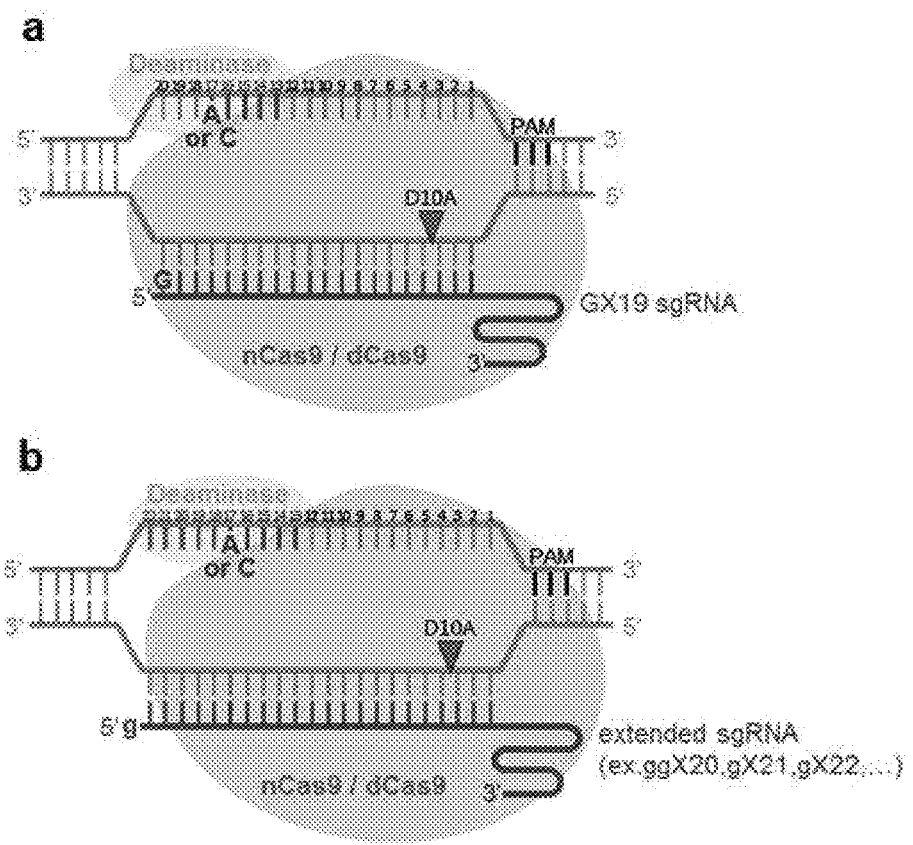
FIG. 1 is a schematic diagram illustrating the operation of a base-editor depending on the length of sgRNA. When using the conventional method GX19 sgRNA(a) and when using extended sgRNA(b), deamination may occur in a single-stranded DNA exposed after binding to a target position. When extended sgRNA is used, single-stranded DNA exposed in the 5' direction from PAM extends, resulting in deamination in a wider range.

As shown in FIG. 1, when using the conventional method GX19 sgRNA(a) and when using extended sgRNA(b), deamination may occur in a single-stranded DNA exposed after binding to a target position. When extended sgRNA is used, single-stranded DNA exposed in the 5' direction from PAM extends, resulting in deamination in a wider range.

A conventionally used sgRNA is GX19 or gX19, using the sequence of 20 nucleotides (nt) in the 5' direction from PAM. In a novel method, experimentation was conducted using an extended sgRNA in the form of ggX20, in which two additional mismatched guanines (G) were added in front of 20 nucleotides in the 5' direction from PAM, or in the form of gX21-gX30 using 21 to 30 nucleotide sequences. As a result of experimentation on the HEK293T cell at the HEK2 site with ABE (adenosine base editor) and extended sgRNA, the conventional GX19 sgRNA showed a mutation in the $13^{th}$ to $17^{th}$ adenosine from PAM, and when gX20/gX21/ gX22 sgRNA was used, the $18^{th}$ and $19^{th}$ adenosines were also changed (see FIGS. 2A, 2B, and 2C). It can be seen that the efficiency of the $18^{th}$ and $19^{th}$ adenosine mutations introduced using gX20/gX21/gX22 sgRNA increased 10-fold or more compared to the efficiency shown in GX19 sgRNA (FIG. 2B). Similarly, as a result of observation at the HBB site with CBE (cytosine base editor) and extended sgRNA, it was found that, when using gX20/gX22 sgRNA, mutations were introduced into cytosine at positions 20, 21 and 23 (see FIGS. 2D, 2E, and 2F). In addition, it was found that, when using the ggX20 sgRNA having additional mismatched guanines, the incidence of mutation by CBE in the cytosine at positions 20 to 23 increased 3-fold or more (see FIG. 3). When CBE and ABE were each tested at four different target sites, the use of the extended sgRNA, instead of GX19 sgRNA, extends the operation range of the base editing to positions 18 to 23, which are regions farther compared to the conventional base-editing range (positions 13 to 17 in the 5' direction from PAM), and increases the efficiency up to 5 to 60 times (see FIG. 4).

In one aspect, the present disclosure is directed to an extended guide RNA hybridizable with a target sequence, the extended guide RNA further including 1 to guanines (G) and 1 to 10 nucleotides (wherein the nucleotide is each independently selected from A, T, C and G) at the 5' end.

The extended guide RNA of the present disclosure may be in the form of a single strand (single guide RNA; sgRNA). The extended guide RNA may further include 1 to 10 nucleotides (wherein each of the nucleotides is independently selected from A, T, C and G, for example, is a sequence complementary with the corresponding DNA target sequence) at the 5' end of a conventional guide RNA, for example, sgRNA (targeting sequence is 20 nt; in particular, the first nucleotide at the 5' end may be guanine (G) that matches (is complementary with) the corresponding DNA target site sequence, or guanine (G) that does not match (is non-complementary with) the same). This extended form of sgRNA can increase the base-editing frequency and/or editing efficiency compared to other types of sgRNA.

In addition, the extended sgRNA may further include one to three guanines (G) that match (are complementary with) the corresponding DNA target sequence, or one to three guanines (G) that do not match (are non-complementary with) the corresponding DNA target sequence at the 5' end. The 1 to 10 random nucleotides additionally included at the 5' end may be complementary with the target DNA sequence of the corresponding target site, and thus the length of a single-stranded DNA exposed in the 5' direction from PAM at the target site can be increased to enable gene editing (deamination) to occur over a wider range (for example, mutations (base editing) can be introduced even at positions 18-30 nt or 18-22 nt in the 5' direction from the PAM at the target site) (See FIG. 1B).

Thus, in one aspect, the present disclosure is directed to a composition for base editing including (i) a deaminase or a gene encoding the same, (ii) an RNA-guided engineered nuclease or a gene encoding the same, and (iii) an extended guide RNA hybridizable with the target sequence or a gene encoding the same.

In an embodiment of the present disclosure, a composition for base editing including (1) a deaminase or a gene encoding the same, (2) a target-specific nuclease (RNA-guided engineered nuclease) or a gene encoding the same, and (3) a guide RNA hybridizable with (or having a nucleotide sequence complementary with) a target site of a target gene, or DNA encoding the same (or a recombinant vector including the DNA). At this time, the guide RNA, as described above, may be extended guide RNA that further includes 1 to 10 nucleotides (wherein each nucleotide is independently selected from A, T, C and G, for example, is a complementary sequence with the corresponding DNA target sequence) at the 5' end of a conventional guide RNA, for example, sgRNA, and may further include one to three matched or mismatched guanines (G) at the 5' end of sgRNA.

The composition for base editing may have base-editing (e.g., base substitution) activity in eukaryotic cells. The eukaryotic cells may be cells of eukaryotic animals, such as embryonic cells, or cells of eukaryotic plants (e.g., algae, monocotyledonous plants, dicotyledonous plants, etc.), and in one specific example, the eukaryotic cells may be mammalian cells, such as mammalian embryonic cells or eukaryotic plant cells. The coding gene used herein may be used in the form of cDNA, rDNA, a recombinant vector containing the same, or mRNA.

"Deaminase" broadly refers to enzymes having activity of removing an amine group from a specific base in eukaryotic cells, and may be, for example, a cytidine deaminase and/or adenosine deaminase that converts cytidine to uridine. In one example, the deaminase may include one or more selected from the group consisting of apolipoprotein B editing complex 1 (APOBEC1), activation-induced deaminase (AID), and tRNA-specific adenosine deaminase (tadA), but is not limited thereto. A single nucleotide substitution in eukaryotic cells can be induced by such base conversion (e.g., conversion of cytidine to uridine).

In one example, in addition to (1) a deaminase or a gene encoding the same (recombinant vector containing mRNA or coding DNA), (2) an RNA-guided engineered nuclease or a gene encoding the same (recombinant vector containing mRNA or coding DNA), and (3) an extended guide RNA or a gene (DNA) encoding the same, the composition for base editing may further include (4) a uracil DNA glycosylase inhibitor (UGI) or a gene encoding the same and/or (5) a nuclear localization sequence (NLS) or a gene encoding the same.

In the composition for base editing of the present disclosure, when the deaminase, RNA-guide engineered nuclease, and optionally a UGI and/or NLS-linked fusion protein or a fusion gene linked to a coding gene thereof is used, at least one suitable linker (a peptide linker (3-30 or 3-20 amino acids) in the case of fusion proteins, and an oligonucleotide linker (9 to 90 or 9-60 nt) in the case of fusion genes may be further included in one or more between proteins or genes, for example, between the deaminase and the RNA-guide engineered nuclease, the nuclease and UGI, and between UGI and NLS.

In one example, the RNA-guide engineered nuclease may be a modified RNA-guide engineered nuclease modified to eliminate the gene double-strand cleavage activity thereof.

The modified RNA-guide engineered nuclease may be a modified Cas9 (CRISPR-related protein 9) system or a modified Cpf1 (CRISPR derived from *Prevotella* and *Francisella* 1) system modified to cut (formation of nick) one strand of the target gene. In one example, the modified RNA-guide engineered nuclease may be selected from the group consisting of Cas9 nickase (nCas9), catalytically deficient Cas9 (dCas9) and the like.

In the present disclosure, when the composition for base editing includes a deaminase-coding gene and an RNA-guide nuclease-coding gene, the coding gene may be coding DNA or mRNA. In addition, the deaminase-coding gene and the RNA-guided engineered nuclease-coding gene are included in the form of mRNA, or a recombinant vector including the gene (DNA) in separate vectors (i.e., a recombinant vector including deaminase-encoding DNA and a recombinant vector including DNA-guided nuclease-encoding DNA), or in the form of a recombinant vector including the genes (DNAs) in one vector.

The guide RNA may be a double guide RNA including CRISPR RNA (crRNA), trans-activating crRNA (tracrRNA), crRNA and tracrRNA (a complex of crRNA and tracrRNA), or single guide RNA (sgRNA). In one example, the composition for base editing may include ribonucleoprotein (RNP), which includes mRNA encoding a deaminase and a modified RNA-guide nuclease, and guide RNA, or includes a deaminase and a modified RNA-guide nuclease and guide RNA. The ribonucleoprotein may include a mixture of a deaminase, a modified RNA-guide nuclease and a guide RNA, or may include a complex of a deaminase, a modified RNA-guide nuclease and a guide RNA.

In another aspect, the present disclosure provides a method for base editing including introducing the composition for base editing into cells.

In another aspect, the present disclosure provides a method for base editing including introducing the composition for base editing into cells. The cells may be eukaryotic cells, and the base-editing method may be carried out by conducting base editing (e.g., base substitution) in eukaryotic cells.

The eukaryotic cells may be cells of eukaryotic animals, such as embryonic cells of eukaryotic animals, and/or cells of eukaryotic plant, and in one specific example, the eukaryotic cells may be mammalian cells, such as mammalian embryonic cells, and/or eukaryotic plant cells. The base-editing method is capable of obtaining a base conversion rate (base substitution rate) of 40% or more, 45% or more, 50% or more, 55% or more, 60% or more, 65% or more, 70% or more, 75% or more, 80% or more, 85% or more, 90% or more, 95% or more, 97% or more, 99% or more, or 100% in eukaryotic cells (e.g., eukaryotic embryonic cells and/or eukaryotic plant cells). In addition, the base-editing method can induce a variety of mutants by generating a termination codon in a gene (e.g., a coding sequence) through base substitution to knock out the gene, or introducing a mutation into a non-coding DNA sequence that does not produce a protein.

Figure 5A:
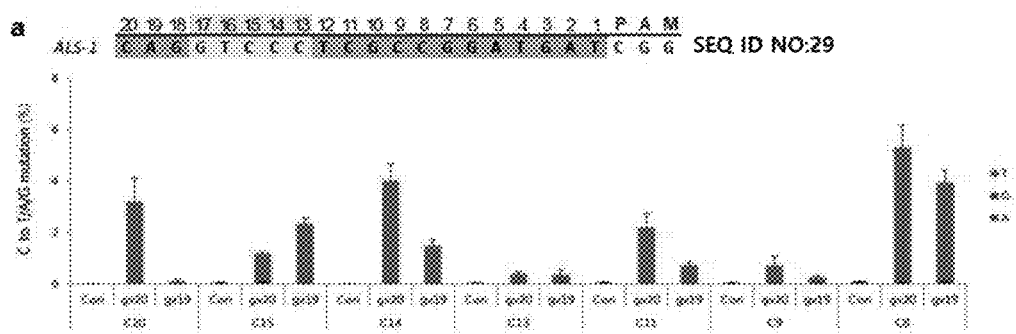
FIG. 5A shows the substitution efficiency depending on the cytosine position when gX19 sgRNA and gX20 sgRNA were used along with the AID2 cytosine base-editor in the rapeseed protoplast.

In one aspect of the present disclosure, whether base editing is possible in a wider range by increasing the length of the sgRNA based thereon was examined in rapeseed (*Brassica napus*) and soybean (*Glycine max*). In the protoplast derived from the cotyledon of *Brassica napus*, gX19 and gX20 sgRNA, capable of targeting the ALS gene, which is a herbicide resistance gene, were transfected into AID2 Base-Edito. As a result, when the gX20 sgRNA was used, the cytosine at position 20 was changed to thymine (FIG. 5A). Only in this case was a STOP codon produced, whereby the corresponding gene was knocked out (FIG. 5B). When transfection was performed on the protoplast obtained from the callus of soybean as another crop to target the ALS gene, the efficiency of conversion of cytosine at the position 20 to thymine was increased when gX20 sgRNA was used (see FIGS. 5C and 5D). Finally, ABE was used to introduce an H420R substitution known as an albinism-causing mutation into the mouse tyrosinase gene. As a result of conducting analysis in the blastocyst stage after performing microinjection into the mouse embryo along with ABE mRNA, while changing the form of sgRNA targeting tyrosinase, the efficiency of changing adenosine at position 18 was found to increase when GX20 or GX21 sgRNA was used rather than gX19 (FIG. 6A). In order to introduce the desired H420R mutation, the adenosine at position 18 should be changed. Thus, a mouse pup was obtained using GX21 sgRNA, which is capable of changing the corresponding position at the highest efficiency. Among them, three pups were found to have the H420R mutation (FIG. 6B). As described above, when it is necessary to edit the base in the 5' direction outside the conventional base-editing window, it was found that it is more efficient to use extended sgRNA than general GX19 sgRNA.

In another aspect, the present disclosure provides a method for producing a mutant adult of a mammal other than a human, or an eukaryotic plant including (a) introducing the composition for base editing into a mammalian embryo or a eukaryotic plant embryo and (b) growing the embryo to obtain an adult.

In particular, the composition for base editing of the present disclosure can be usefully applied to the production of a mammalian or eukaryotic plant adult in which a desired gene is inactivated or a desired mutation is induced by applying the composition to a mammalian embryo or a eukaryotic plant embryo.

The step of introducing the composition for base editing into the cells includes introducing a deaminase or deaminase-encoding gene, a RNA-guide nuclease or RNA-guide-nuclease-encoding gene, and an extended guide RNA or extended-guide-RNA-encoding gene into the cell. One or more of the coding genes may be introduced in the state of being included in separate recombinant vectors or a single recombinant vector.

In one example, the step of introducing the composition for base editing into the cells may be carried out in the following manner:

1) transfecting the cells with a recombinant vector including one or two or more of the deaminase-encoding DNA, RNA-guided engineered nuclease-encoding DNA, and extended guide RNA-encoding gene, 2) directly injecting, into the cells, a deaminase, an RNA-guide nuclease and an extended guide RNA (e.g., ribonucleoprotein in the form of a mixture or complex containing a deaminase, an RNA-guide nuclease, and an extended guide RNA), or 3) directly injecting, into the cells, each of a deaminase-encoding mRNA, an RNA-guide nuclease-encoding mRNA and a guide RNA, or a mixture thereof.

"Direct injection" means that the deaminase, RNA-guided engineered nuclease, and extended guide RNA (e.g., ribonucleoprotein in the form of a mixture or complex containing a deaminase, an RNA-guided engineered nuclease, and an extended guide RNA of 2), or the deaminase-encoding mRNA, RNA-guided engineered nuclease-encoding mRNA and extended guide RNA of 3), pass through the cell membrane and/or nuclear membrane without using a recombinant vector, and then are delivered to the genome, and may be performed by, for example, electroporation, lipofection, microinjection, or the like.

In another aspect, the present disclosure provides a genetically modified cell including a base edited by the base-editing method. The genetically modified cell may be a cell in which a base substitution, for example, a single base substitution or a point mutation, occurs in the target gene due to the base editing. The cell may be a eukaryotic cell. The eukaryotic cell may be a eukaryotic animal cell such as an embryonic cell, and/or a eukaryotic plant cell, and in one embodiment, mammalian cells including or excluding humans, such as mammalian embryonic cells including or excluding humans, and/or eukaryotic plant cells.

In another aspect, the present disclosure provides a method for producing a genetically modified animal including transplanting a mammalian embryo injected with the composition for base editing or a genetically modified mammalian embryo including a base edited by the base-editing method into a fallopian tube of a mammal to produce a genetically modified animal. The genetically modified mammal may be an animal derived from an embryo having a base substitution, for example, a single base substitution or a point mutation in the target gene, due to the base editing.

The mammal into the fallopian tube of which the embryonic cell is transplanted may be a mammal (consigner) of the same species as the mammal from which the embryonic cell is derived.

In another aspect, the present disclosure provides a genetically modified animal derived from the genetically modified cell. The genetically modified animal may be produced by the method for producing the genetically modified animal. The animal may be a eukaryotic animal, such as a mammal, including human or non-human.

The cells to which the composition for base editing is applied herein may be eukaryotic cells, such as eukaryotic animal cells. The eukaryotic animal may be a mammal including a primate such as a human or a rodent such as a mouse. The eukaryotic animal cell may be a mammalian embryo. For example, the embryo may be a fertilized embryo obtained by crossing a male mammal with a hyper-ovulation-induced female mammal (e.g., inducing hyper-ovulation by injecting a gonadal hormone such as pregnant mare serum gonadotropin (PMSG) or human chorionic gonadotropin (hCG), wherein the fertilized embryo may be collected from the fallopian tube of the female mammal. The embryo to which the composition for base editing is applied (injected) may be a fertilized 1-cell-stage embryo (zygote).

As used herein, the term "base editing" refers to a base mutation (substitution, deletion or addition) causing a point mutation (such as a single amino acid mutation due to a gene or a gene-level point mutation) at a target site within a target gene, and is distinguished from gene editing, which involves mutation of a relatively large number of bases, in that only a few bases (one or two bases, for example, one base) are mutated. The base editing may not involve double-stranded DNA cleavage of the gene.

According to the composition or method for base editing provided herein, base editing (basic modification or base substitution; mutation by deamination of A or C) may occur in the strand (that is, a strand in which a PAM sequence is located) opposite the nicked DNA strand (strand opposite the strand in which the PAM sequence is located, strand to which guide RNA binds (hybridizes)). When using a guide RNA with a normal length, for example, base editing (base modification or base substitution) occurs in the nucleotide at position 17 in the 5' direction from PAM, but when using the extended guide RNA provided herein, base editing may also occur in the region after the position 17 in the 5' direction from the PAM, for example, in the extended ranges corresponding to positions from 18 to 30, positions from 18 to 25, or positions from 18 to 22 in the 5' direction from the PAM.

As used herein, the term "basic mutation (or base substitution)" means that a mutation (e.g., substitution) has occurred in a nucleotide including a base, and can be used interchangeably with "nucleotide mutation (or nucleotide substitution)", and such a base mutation may occur in one or both alleles.

In one example, the base mutation or base editing involving the same may be carried out through a variety of methods, for example, by knocking out the target gene or introducing a mutation into the non-coding DNA sequence that does not produce proteins by producing a termination codon at a target site, or producing a codon encoding an amino acid different from a wild type, but is not limited thereto.

In the present disclosure, the base editing or base mutation may be performed in vitro or in vivo.

As used herein, the term "base sequence" refers to a sequence of a nucleotide containing a corresponding base, and may be used interchangeably with "nucleotide sequence" or "nucleic acid sequence".

As used herein, the term "target gene" refers to a gene which is the subject on which base editing (or base mutation) is conducted, and the term "target site" or "target region" means a site where base editing is caused by a target-specific nuclease in a target gene. For example, when the target-specific nuclease includes an RNA-guided engineered nuclease (RGEN), the target site means a gene site (either a double strand or any single one of a double strand) that is located adjacent to the 5' end and/or the 3' end of the sequence (PAM sequence) recognized by the RNA-guided engineered nuclease (RGEN) in the target gene, and has a maximum length of about 50 bp or about 40 bp.

In one example, when the target-specific nuclease includes an RNA-guided engineered nuclease, it may further include a guide RNA including a targeting sequence along with the RNA-guided engineered nuclease. The term "targeting sequence" may refer to a site of guide RNA including a base sequence complementary (hybridizable) to a base sequence of a region containing about 20 nucleotides (nt) that is continuous in the target region. The extended guide RNA described herein further includes 1 to 10 additional optional nucleotides (wherein the nucleotide is selected from A, T, C and G; for example, may be complementary to the corresponding target sequence) at the 5' end and/or may include 1 to 3 additional matched or mismatched guanines at the 5' end. The 1 to 10 additional arbitrary nucleotides at the 5' end may be a sequence complementary to the sequence of the extended target DNA region corresponding thereto, whereby the length of single-stranded DNA in which the PAM is exposed in the 5' direction in the target region can be increased to allow for gene editing (deamination) over a wider range.

In the present disclosure, the base sequence of the target site including the base sequence complementary to the targeting sequence may be referred to as a "target sequence", and the target sequence may be a continuous base sequence with a length of about 20 nt or a site corresponding to the strand complementary thereto that is located adjacent to the 5' end and/or 3' end of the PAM sequence recognized by the RNA-guided engineered nuclease (RGEN).

The deaminase refers to an enzyme having activity of removing an amine group from a specific base in eukaryotic cells, and may be, for example, a cytidine deaminase and/or adenosine deaminase that converts cytidine to uridine. In one example, the deaminase may include one or more selected from the group consisting of APOBEC (apolipoprotein B mRNA editing enzyme, catalytic polypeptide-like enzyme), AID (activation-induced deaminase), tadA (tRNA-specific adenosine deaminase) and the like, but is not limited thereto. The APOBEC1, AID, and tadA may be derived from a prokaryotic animal such as *E. coli*, or may be derived from a eukaryotic animal such as a primate, including a human, or a mammal such as a rodent, including a mouse.

The deaminase may be used in the form of a protein, a gene (e.g., DNA or mRNA) encoding the same, or a recombinant vector containing the gene. As used herein, the target-specific nuclease is also called a "genetic editor" (programmable nuclease) and collectively refers to a nuclease (e.g., endonuclease) capable of recognizing and cleaving (single-strand or double-strand cleaving) a specific site on a desired genomic DNA.

For example, the target-specific nuclease may be one or more selected from all nucleases that recognize a specific sequence of a target gene and cause insertion and/or deletion (Indel) in the target gene due to the nucleotide cleavage activity thereof.

For example, the target-specific nuclease may include one or more selected from the group consisting of RGEN (RNA-guided engineered nuclease; e.g., Cas protein (e.g., Cas9), Cpf1 or the like) derived from CRISPR, which is a microbial immune system, but is not limited thereto.

The target-specific nuclease may recognize a specific nucleotide sequence in the genome of prokaryotic cells and/or animal and plant cells (e.g., eukaryotic cells) including human cells to cause a double-strand break (DSB). The double-strand break can form a blunt end or cohesive end by breaking a double helix of the DNA. The DSB can be efficiently repaired in cells by homologous recombination or non-homologous end-joining (NHEJ) mechanisms. During this process, desired mutations can be introduced into the target site.

For example, the target-specific nuclease may include one or more selected from the group consisting of nucleases (e.g., endonucleases) involved in type II and/or type V CRISPR systems, such as Cas protein (e.g., Cas9 protein (CRISPR (clustered regularly interspaced short palindromic repeats) associated protein 9)), and Cpf1 protein (CRISPR from *Prevotella* and *Francisella* 1). In this case, the target-specific nuclease further includes a target-DNA-specific guide RNA to guide the target site of genomic DNA. The guide RNA may be transcribed in vitro, and may be, for example, transcribed from a double-stranded oligonucleotide or a plasmid template, but is not limited thereto. The target-specific nuclease can act as a ribonucleoprotein (RNP) by forming a ribonucleic acid-protein complex bound to guide RNA (RNA-guided engineered nuclease) after being delivered to cells in vitro or in vivo. Cas protein is a major protein component of the CRISPR/Cas system, and is a protein capable of forming an activated endonuclease or nickase.

Cas protein or gene information can be obtained from a known database such as GenBank of the National Center for Biotechnology Information (NCBI). For example, the Cas protein may include one or more selected from the group consisting of Cas9 proteins derived from *Streptococcus* sp., for example, *Streptococcus pyogenes*, Cas9 protein (e.g., SwissProt Accession number Q99ZW2 (NP_269215.1)); Cas proteins derived from *Campylobacter* sp., for example *Campylobacter jejuni*, Cas proteins derived from *Streptococcus* sp., such as *Streptococcus thermophiles* or *Streptococcus aureus*, Cas9 proteins derived from *Neisseria meningitidis*, Cas proteins derived from *Pasteurella* sp., such as *Pasteurella multocida*, and Cas9 proteins derived from *Francisella* sp., for example, *Francisella novicida*, but is not limited thereto.

In the present disclosure, the Cpf1 protein is an endonuclease of a new CRISPR system that is distinguished from the CRISPR/Cas system, is relatively small in size compared to Cas9, does not require tracrRNA, and can act by a single guide RNA. In addition, the Cpf1 protein recognizes a thymine-rich protospacer-adjacent motif (PAM) sequence and cuts a double chain of DNA to produce a cohesive end (cohesive double-strand break).

For example, the Cpf1 protein may be derived from Candidatus sp., Lachnospira sp., Butyrivibrio sp., Peregrinibacteria sp., Acidaminococcus sp., Porphyromonas sp., Prevotella sp., Francisella sp., Candidatus Methanopiasma, or Eubacterium sp., example, microorganisms such as Parcubacteria bacterium (GWC2011_GWC2_44_17), Lachnospiraceae bacterium (MC2017), Butyrivibrio proteoclasticus, Peregrinibacteria bacterium (GW2011_GWA_33-10), Acidaminococcus sp. (BV3L6), Porphyromonas macacae, Lachnospiraceae bacterium (ND2006), Porphyromonas crevioricanis, Prevotella disiens, Moraxella bovoculi (237), Smithella sp. (SC_KO8D17), Leptospira inadai, Lachnospiraceae bacterium (MA2020), Francisella novicida (U112), Candidatus Methanoplasma termitum, Candidatus paceibacter, and Eubacterium eligens, but the present disclosure is not limited thereto.

The target-specific nuclease may be isolated from a microorganism or may be artificially or non-naturally obtained through a method such as a recombinant method or a synthetic method. The target-specific nuclease may be pre-transcribed mRNA or a protein produced in advance in vitro, or may be included in a recombinant vector for expression in vivo in a target cell. In one example, the target-specific nuclease (e.g., Cas9, Cpf1, etc.) may be a recombinant protein produced by recombinant DNA (rDNA). The recombinant DNA refers to a DNA molecule artificially produced by a genetic recombination method such as molecular cloning to include a heterogeneous or homogeneous genetic material obtained from various organisms. For example, when recombinant DNA is expressed in an appropriate organism to produce a target-specific nuclease (in vivo or in vitro), the recombinant DNA may have a nucleotide sequence reconstituted by selecting a codon optimized for expression in the organism, among codons encoding proteins to be produced.

The target-specific nuclease used herein may be a mutated form of a mutated target-specific nuclease. The mutated target-specific nuclease may mean a nuclease mutated to lose an endonuclease activity that cuts the DNA double strand, for example, may include at least one selected from mutated target-specific nucleases that are mutated to lose endonuclease activity and have nickase activity, and mutated target-specific nucleases that are mutated to lose both endonuclease activity and nickase activity.

When the mutated target-specific nuclease has nickase activity, a nick may be introduced into the strand where the base editing occurs or the strand opposite thereto, simultaneously or sequentially, regardless of the sequence, with the base conversion by a deaminase (e.g., conversion of cytidine to uridine) (for example, in the strand opposite the strand in which the PAM is located, the nick is introduced between the third nucleotide and the fourth nucleotide in the 5'-end direction of the PAM sequence). The mutations (e.g., amino acid substitutions) of the target-specific nuclease may occur in at least the catalytically active domain of the nuclease (for example, the RuvC catalytic domain in the case of Cas9). In one example, when the target-specific nuclease is a Streptococcus pyogenes-derived Cas9 protein (SwissProt Accession number Q99ZW2 (NP_269215.1)), the mutation may include a mutation in the form of a substitution of at least one selected from the group consisting of a catalytic aspartate residue having catalytic activity (aspartate at position 10 (D10)), glutamate at position 762 (E762), histidine at position 840 (H840), asparagine at position 854 (N854), asparagine at position 863 (N863), aspartate at position 986 (D986), and the like, with any other amino acid. In this case, the substituted any other amino acid may be alanine, but is not limited thereto.

In another example, the mutated target-specific nuclease may be mutated to recognize a PAM sequence different from the wild-type Cas9 protein. For example, the mutated target-specific nuclease may be mutated to recognize NGA (wherein N is any base selected from A, T, G and C) different from the PAM sequence (NGG) of wild-type Cas9 by substituting at least one, for example, three, of aspartate at position 1135 (D1135), arginine at position 1335 (R1335), and threonine at position 1337 (T1337) of the Cas9 protein derived from Streptococcus pyogenes with other amino acid.

In one example, the mutated target-specific nuclease may have an amino acid substitution in the following region of the amino acid sequence of the Streptococcus pyogenes-derived Cas9 protein:

(1) D10, H840, or D10+H840;
(2) D1135, R1335, T1337, or D1135+R1335+T1337; or
(3) both residues (1) and (2).

As used herein, the term "other amino acid" means an amino acid selected from amino acids other than the amino acid that a wild-type protein has in the original mutation position thereof, among alanine, isoleucine, leucine, methionine, phenylalanine, proline, tryptophan, valine, asparagine, cysteine, glutamine, glycine, serine, threonine, tyrosine, aspartate, glutamate, arginine, histidine, lysine, and all known variants of the above amino acids. For example, the "other amino acid" may be alanine, valine, glutamine, or arginine.

In one example, the mutated target-specific nuclease may recognize a PAM sequence different from wild-type Cas9 or a modified Cas9 protein that loses endonuclease activity (e.g., has nickase activity, or loses both endonuclease activity and nickase activity). For example, the modified Cas9 protein is, in the Cas9 protein derived from Streptococcus pyogenes:

(1) a modified Cas9 protein that loses endonuclease activity and has nickase activity due to the introduction of a mutation (e.g., substitution with other amino acid) at the position D10 or H840, or a Cas9 protein that loses both endonuclease activity and nickase activity due to the introduction of a mutation (e.g., substitution with other amino acid) at the position D10 or H840 into the Cas9 protein derived from Streptococcus pyogenes;

(2) a modified Cas9 protein that recognizes a PAM sequence different from the wild type due to introduction of a mutation (e.g., substitution with other amino acids) in one or more or all of D1135, R1335 and T1337; or (3) a modified Cas9 protein that has nickase activity and recognizes a PAM sequence different from a wild type, or loses both endonuclease activity and nickase activity and recognizes a PAM sequence different from a wild type due to the introduction of mutations of (1) and (2).

For example, the mutation at the position D10 of the CAs9 protein may be a D10A mutation (meaning that the $10^{th}$ amino acid (D) of the Cas9 protein amino acid is substituted with (A); hereinafter, the mutation introduced into Cas9 may be represented in the same manner as above), the mutation at the position H840 may be represented by "H840A mutation", and the mutations at positions D1135, R1335 and T1337 may be represented by D1135V, R1335Q and T1337R, respectively.

As used herein, the term "nuclease" means "target-specific nuclease" such as Cas9 or Cpf1 as described above, unless stated otherwise.

The nuclease may be isolated from a microorganism, or may be artificially or non-naturally obtained through a method such as a recombinant method or a synthetic method. In one example, the nuclease (e.g., Cas9, Cpf1, etc.) may be a recombinant protein produced by recombinant DNA. "Recombinant DNA (rDNA)" refers to a DNA molecule artificially produced by a genetic recombination method such as molecular cloning to contain a heterologous or homologous genetic material obtained from various organisms. For example, when the recombinant DNA is expressed in an appropriate organism to produce a protein (nuclease) (in vivo or in vitro), the recombinant DNA may have a nucleotide sequence reconstituted by selecting a codon optimized for expression in the organism, among codons encoding proteins to be produced.

The nuclease may be used in the form of a protein, a nucleic acid molecule (e.g., DNA or mRNA) encoding the same, a ribonucleoprotein linked to guide RNA, a nucleic acid molecule encoding the ribonucleoprotein, or a recombinant vector containing the nucleic acid molecule.

The deaminase and nuclease and/or nucleic acid molecules encoding the same may be in a form that can be delivered to, acted on and/or expressed in the nucleus.

The deaminase and nuclease may have a form enabling easy introduction into cells. For example, the deaminase and nuclease may be linked to a cell-penetrating peptide and/or protein transduction domain. The protein transduction domain may be poly-arginine or HIV-derived TAT protein, but is not limited thereto. Since various kinds of cell-penetrating peptides or protein transduction domains are known in the art in addition to the examples described above, those skilled in the art will understand that the present disclosure is not limited to the above examples and various examples may be applied.

In addition, the deaminase and nuclease and/or nucleic acid molecules encoding the same may further include a nuclear localization signal (NLS) sequence or a nucleic acid sequence encoding the same. Accordingly, the expression cassette including the deaminase-encoding nucleic acid molecule and/or nuclease-encoding nucleic acid molecule may include regulatory sequences such as a promoter sequence for expressing the deaminase and/or nuclease, and optionally, may further include an NLS sequence (CCCAAGAAGAAGAGGAAAGTC: SEQ ID NO: 61). The NLS sequence is well known in the art.

The deaminase and nuclease and/or the nucleic acid molecule encoding the same may be linked to a tag for isolation and/or purification or to a nucleic acid sequence encoding the tag. For example, the tag may be appropriately selected from the group consisting of small-peptide tags such as His tags, Flag tags and S tags, GST (glutathione S-transferase) tags, and MBP (maltose-binding protein) tags, but is not limited thereto.

In addition, the composition for base editing used herein may further include a uracil DNA glycosylase inhibitor (UGI) or a gene encoding the same (recombinant vector form containing coding DNA or in-vitro-transcribed mRNA form). When the composition for base editing further includes a uracil DNA glycosylase inhibitor, a proportion of a specific base that is substituted using a deaminase (e.g., substitution of C with T by a cytosine deaminase) increases compared to the case without the uracil DNA glycosylase inhibitor, and when the uracil DNA glycosylase inhibitor is not further included, the proportion of base substitutions other than a specific base substitution (e.g., substitution of C with T by cytosine deaminase) increases (i.e., various forms of base substitution occur).

In the present disclosure, the term "guide RNA" refers to RNA including a targeting sequence that can hybridize to a specific base sequence (target sequence) within a target site in a target gene, and binds to a nuclease such as Cas protein or Cpf1 in vitro or in vivo to guide the same to a target gene (or target site). The guide RNA may be appropriately selected according to the type of nuclease to form a complex and/or source microorganisms thereof.

For example, the guide RNA may include at least one selected from the group consisting of:
CRISPR RNA (crRNA) including a site (targeting sequence) hybridizable to a target sequence;
trans-activating crRNA (tracrRNA) including a site that interacts with a nuclease such as Cas protein or Cpf1; and
single guide RNA (sgRNA) fused with the main sites of the crRNA and tracrRNA (e.g., crRNA sites containing a targeting sequence and tracrRNA sites interacting with a nuclease).

Specifically, the guide RNA may be a dual guide RNA including CRISPR RNA (crRNA) and trans-activating crRNA (tracrRNA), or a single guide RNA (sgRNA) including the main sites of crRNA and tracrRNA.

The sgRNA may include a part (also referred to as "spacer region", "target DNA recognition sequence", or "base-pairing region") having a complementary sequence (targeting sequence) to a target gene (target site) in the target sequence, and a hairpin structure for Cas protein binding. More specifically, the sgRNA may include a part having a sequence (targeting sequence) complementary to the target sequence in the target gene, a hairpin structure for Cas protein binding, and a terminator sequence. The structure may be present from 5' to 3', but the present disclosure is not limited thereto. Any type of guide RNA can be used in the present disclosure as the above-described structure, as long as the guide RNA includes main parts of crRNA and tracrRNA and a complementary part to the target DNA.

For example, the Cas9 protein requires two guide RNAs for target gene editing, namely, CRISPR RNA (crRNA) having a nucleotide sequence hybridizable with a target site of the target gene and trans-activating crRNA (tracrRNA) interacting with the Cas9 protein, and these crRNAs and tracrRNAs can be used in the form of a double-stranded crRNA:tracrRNA complex linked to each other, or a single guide RNA (sgRNA) linked through a linker. In one example, when using a Cas9 protein derived from *Streptococcus pyogenes*, the sgRNA may have a hairpin (step-loop) structure formed by all or part of a crRNA including at least a hybridizable nucleotide sequence of the crRNA and all or part of a tracrRNA including at least a site that interacts with the Cas9 protein of the tracrRNA of Cas9 via a nucleotide linker (in this case, the nucleotide linker may correspond to a loop structure).

The guide RNA, specifically crRNA or sgRNA, includes a sequence (targeting sequence) complementary to the target sequence in the target gene, and may include one or more, for example, 1 to 10, 1 to 5 or 1 to 3 additional nucleotides at the upstream region of the crRNA or sgRNA, specifically at the 5' end of the sgRNA or crRNA of dual guide RNA. The additional nucleotide may be guanine (G), but is not limited thereto.

In another example, when the nuclease is Cpf1, the guide RNA may include crRNA, and may be appropriately selected according to the type of Cpf1 protein to form a complex and/or the source microorganism thereof.

The specific sequence of the guide RNA can be appropriately selected according to the type of nuclease (Cas9 or Cpf1) (i.e., the source microorganism thereof), which can be easily understood by those skilled in the art to which the present disclosure pertains.

In one example, when a Cas9 protein derived from *Streptococcus pyogenes* is used as a target-specific nuclease, the sgRNA can be represented by the following general formula 1:

For example, the guide RNA may be represented by the following general formula (1):

(General formula 1)
(SEQ ID NO. 60)
5'-(N$_{cas9}$)$_1$-(GUUUUAGAGCUA)-(oligonucleotide linker)-(UAGCAAGUUAAAAUAAGGCUAGUCCGUUAUCAACUUGAAAAAGUGGCACCGAGUCGGUGC-3'

In General formula 1 above,

In (N$_{cas9}$)$_1$, N$_{cas9}$ represents a targeting sequence that binds (hybridizes) to a target site of a target gene, and the nucleic acid sequence is determined according to the sequence of the target site (i.e., a sequence that can hybridize to the target site), 1 represents the number of nucleotides included in the targeting sequence, may be 20, and the first nucleic acid from the 5' end may be a guanine that matches the target site sequence (represented by G; target; when the corresponding position of the target site is cytosine (C)) or guanine that does not match the same (represented by g; when the corresponding position of the target site is not cytosine (C)).

The oligonucleotide linker may include 3 to 5 nucleotides, for example, 4 nucleotides, and the nucleotides may be the same as or different from each other, and may be each independently selected from the group consisting of A, U, C and G.

For example, the case wherein N$_{cas9}$ consists of a total of 20 nucleotides may be represented by "X20" (the number after X (wherein X is selected from A, T, C, and G) represents the number of arbitrary nucleotides), or the case wherein a guanine that matches the first nucleic acid from the 5' end is located may be represented "GX19", and the case wherein a guanine that does not match the first nucleic acid from the 5' end is located may be represented by "gX19".

The sgRNA may further include a termination site including 5 to 7 uracils (U) at the 3' end.

The extended guide RNA may further include 1 to nucleotides at the 5' end of the sgRNA of General Formula 1 described above. Each of the further included nucleotides may be independently selected from A, T, C and G. In this case, the additionally included nucleotides may have a sequence complementary to nucleotides at a corresponding position (extended position) of the target DNA sequence.

In addition, the sgRNA may further include 1 to 3 guanines (G) at the 5' end. In this case, each of the additionally included guanines may independently be complementary to (match) or non-complementary to (mismatch) the nucleotide at the corresponding position of the target sequence.

As described above, compared to the sgRNA of the general Formula 1 described above, for example, X20, GX19, or gX19, an extended sgRNA that further includes 1 to 3 guanines (G) at the 5' end and/or 1 to 10 nucleotides (wherein the nucleotides may be each independently selected from A, T, C and G) at the 5' end of the crRNA or sgRNA can increase the frequency and/or efficiency of base editing and induce base editing in a more extensive area.

The target sequence of the guide RNA may be a continuous nucleic acid sequence located adjacent to a 5' end of PAM on a strand in which a PAM (protospacer adjacent motif) sequence (5'-NGG-3' (N is A, T, G, or C) in the case of *S. pyogenes* Cas9) on the target DNA is located or an opposite strand (complementary strand).

The targeting sequence of the guide RNA capable of hybridizing with the target sequence of the guide RNA means a nucleotide sequence having a sequence homology of 50% or more, 60% or more, 70% or more, 80% or more, 90% or more, 95% or more, 99% or more, or 100% with the nucleotide sequence of a strand complementary to the DNA strand (i.e., DNA strand or opposite strand in which the PAM sequence (5'-NGG-3' (wherein N is A, T, G, or C)) is located and can complementarily bind to the nucleotide sequence.

In the present specification, the nucleic acid sequence of the target site is represented by the nucleic acid sequence of the strand where the PAM sequence is located, among the two DNA strands of the corresponding gene site of the target gene. At this time, the DNA strand to which the guide RNA actually binds is a strand complementary to the strand in which the PAM sequence is located, so the targeting sequence included in the guide RNA has the same nucleic acid sequence as the sequence of the target site, except that T is changed to U due to the characteristics of RNA. Thus, in the present specification, the targeting sequence of the guide RNA and the sequence of the target site (or the sequence of the cleavage site) are represented by the same nucleic acid sequence except that T and U are mutually interchanged.

The guide RNA may be used in the form of RNA (or present in the composition), or may be used in the form of a plasmid containing DNA encoding the same (or present in the composition).

EXAMPLES

Hereinafter, the present disclosure will be described in more detail with reference to the following examples. However, it will be obvious to those skilled in the art that the following examples are provided only for illustration of the present disclosure and should not be construed as limiting the scope of the present disclosure based on the subject matter of the present disclosure.

Example 1: Test of Change of Base-Editing Window Depending on sgRNA Length

Each activity in the HEK293T cell line was measured by deep sequencing. The results are shown in FIGS. 2A to 2F.

Figure 2A:
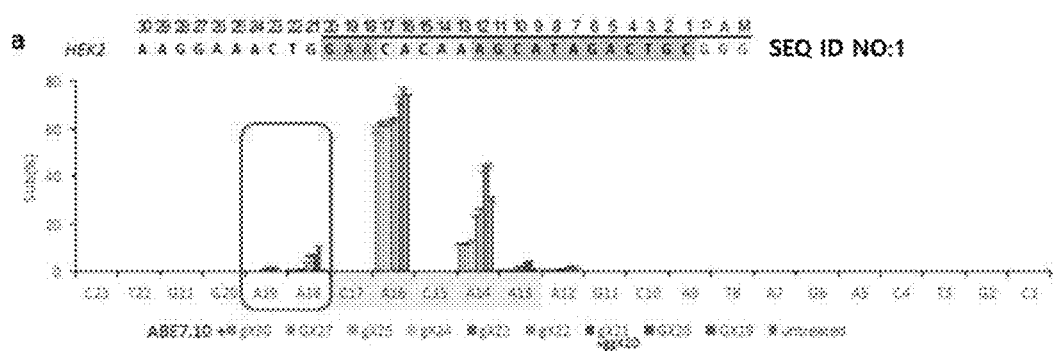
FIG. 2A is a graph showing the ABE 7.10 substitution activity at different base positions depending on the sgRNA length at the HEK2 site.
Figure 2B:
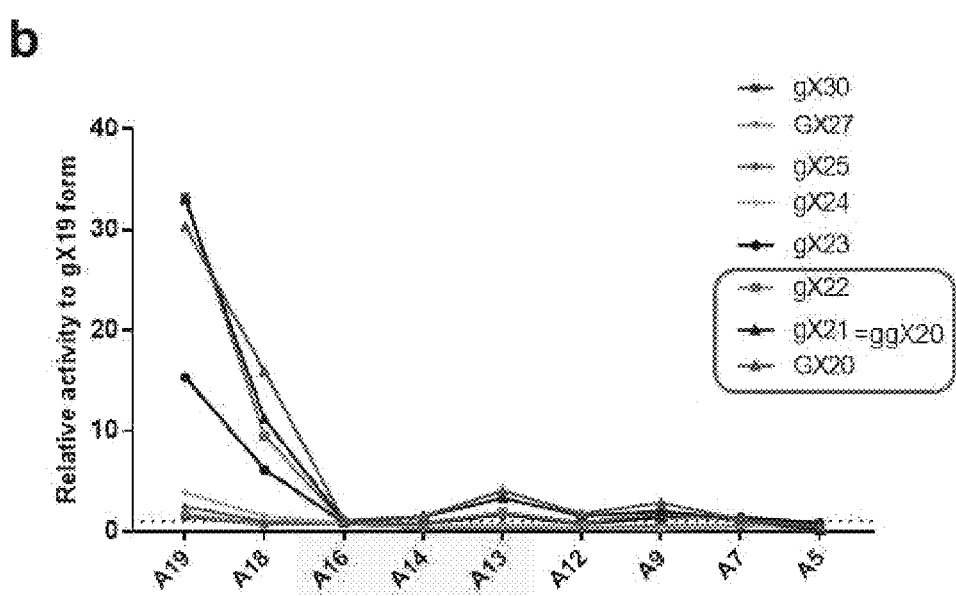
FIG. 2B is a graph showing relative substitution activity [gX20~30 activity/ GX19 activity] compared to the case in which GX19 sgRNA is used.
Figure 2D:
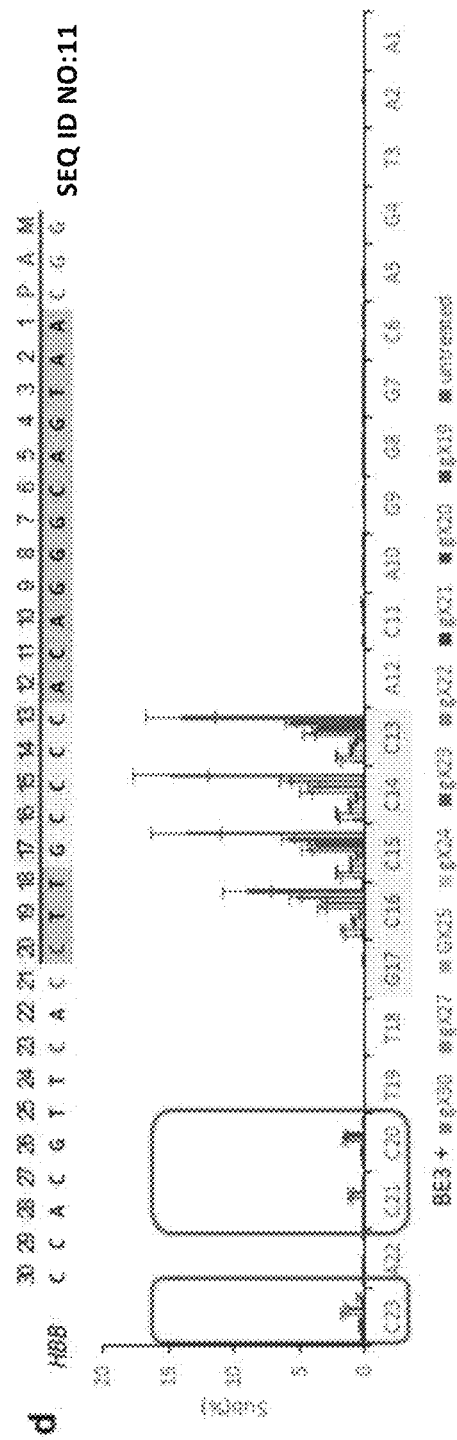
FIG. 2D shows the BE3 substitution activity at different base positions depending on sgRNA length at the HBB site.
Figures 2E, 2F:
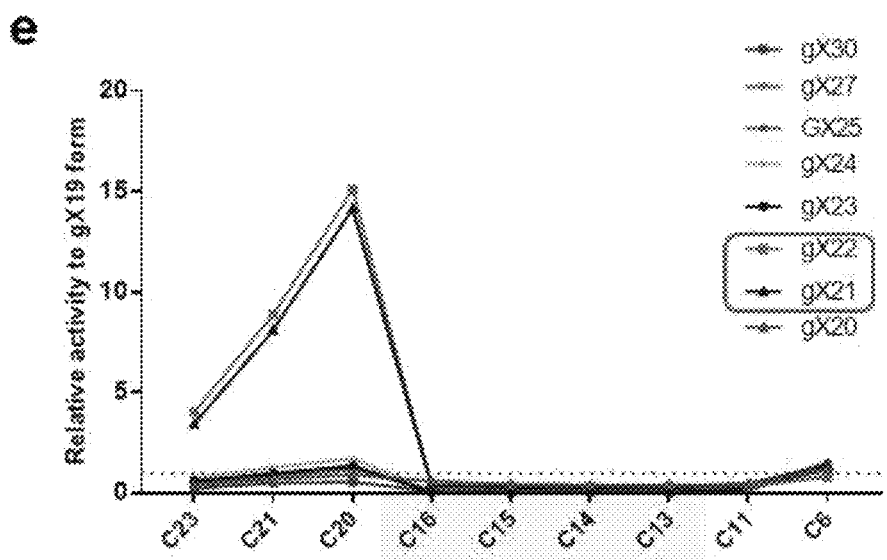
FIG. 2E shows the relative substitution activity [gX20~30 activity/ GX19 activity] compared to the case in which GX19 sgRNA is used.
FIG. 2F shows the most frequently observed mutation allele, wherein the portion in which the mutation was introduced in the WT sequence is expressed in red, and the base-editing window known to operate efficiently when using GX19 sgRNA is expressed in light blue.

FIG. 2A shows the ABE 7.10 substitution activity at different base positions depending on the sgRNA length at the HEK2 site. FIG. 2B shows relative substitution activity [gX20~30 activity/GX19 activity] compared to the case in which GX19 sgRNA is used. FIG. 2C shows the most frequently observed mutation allele, wherein the portion in which the mutation was introduced in the WT sequence is expressed in red. FIG. 2D shows the BE3 substitution activity at different base positions depending on sgRNA length at the HBB site. FIG. 2E shows the relative substitution activity [gX20~30 activity/GX19 activity] compared to the case in which GX19 sgRNA is used. FIG. 2F shows the most frequently observed mutation allele, wherein the portion in which the mutation was introduced in the WT sequence is expressed in red. The base-editing window known to operate efficiently when using GX19 sgRNA is expressed in light blue.

Example 2: Test of Change of Base-Editing Window when Using sgRNA Containing 1 or 2 Additional Mismatched G Each activity in the HEK293T cell line was measured through deep-sequencing and the results are shown in FIG. 3.

Figure 3A:
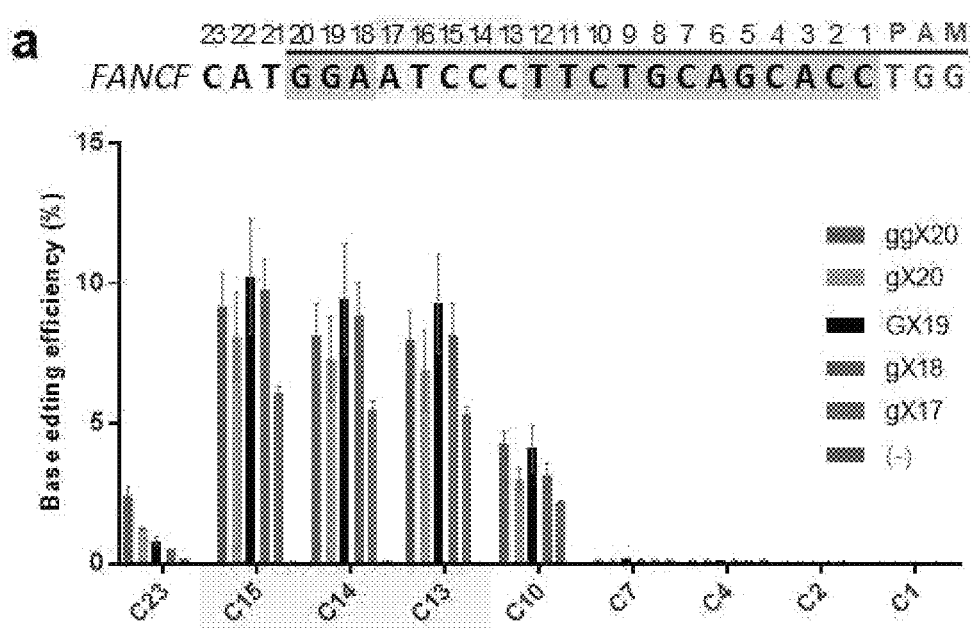
FIGS. 3A and 3C are graphs showing that BE3 substitution activity at different base positions depending on the sgRNA length at the FANCF site (a) and HBB site (c)
Figure 3B:
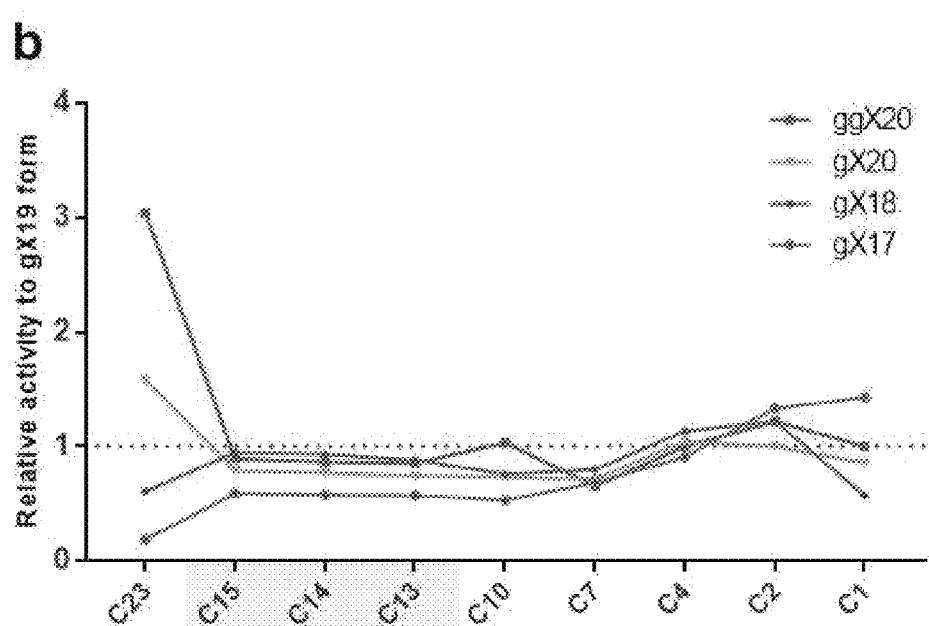
FIGS. 3B and 3D are graphs showing the relative substitution activity [gX20~30 activity/GX19 activity] in the FANCF site (b) and the HBB site (d) compared to when GX19 sgRNA was used.
Figure 3C:
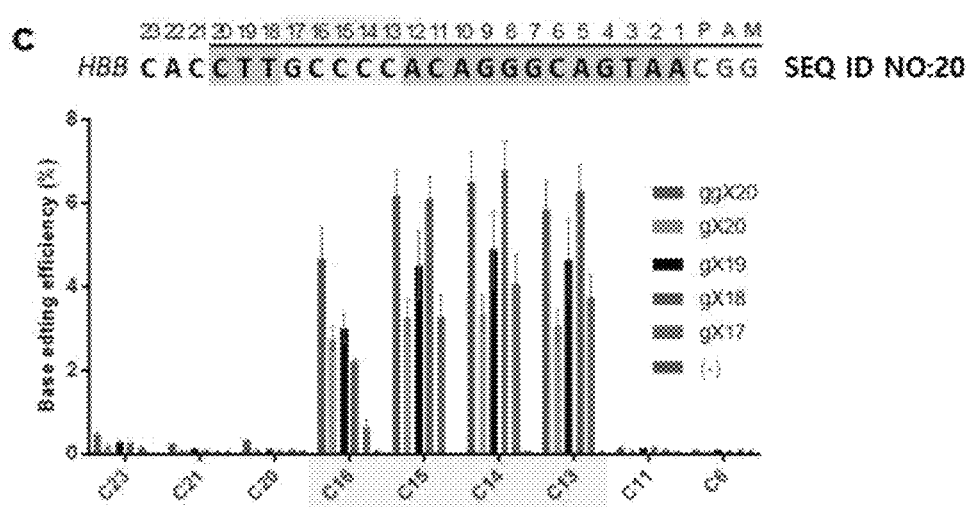
Figure 3D:
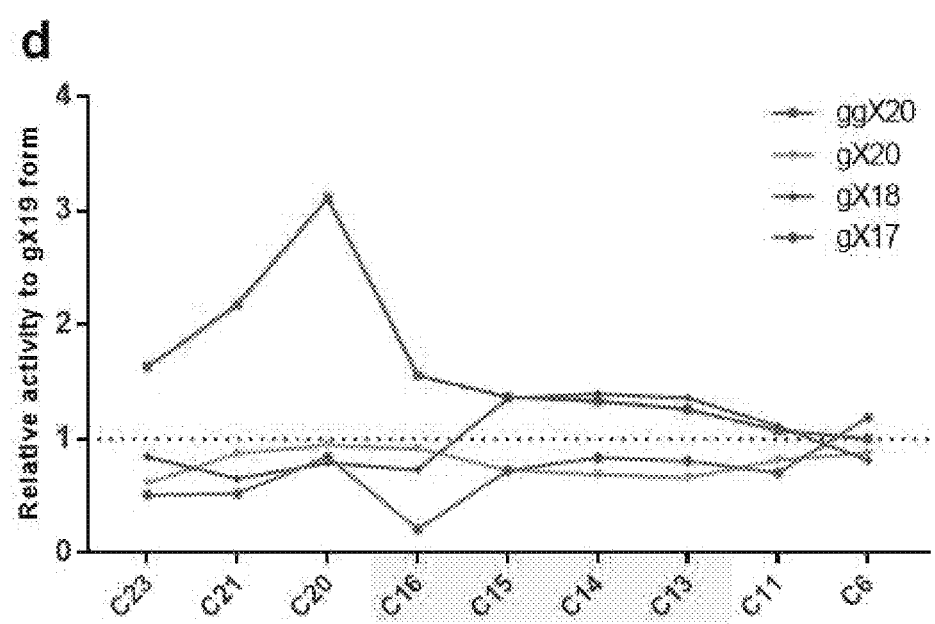

The BE3 substitution activity at different base positions depending on the sgRNA length was shown at the FANCF site (FIG. 3A) and HBB site (FIG. 3C). The relative substitution activity [gX20~30 activity/GX19 activity] was shown in the FANCF site (FIG. 3B) and HBB site (FIG. 3D) compared to when GX19 sgRNA was used.

Example 3: Test of Change of Base-Editing Window Depending on sgRNA Length at Four Different Sites The change of the base-editing window depending on the length of the sgRNA at four different sites was tested, and the results are shown in FIGS. 4A and 4B.

Figure 4A:
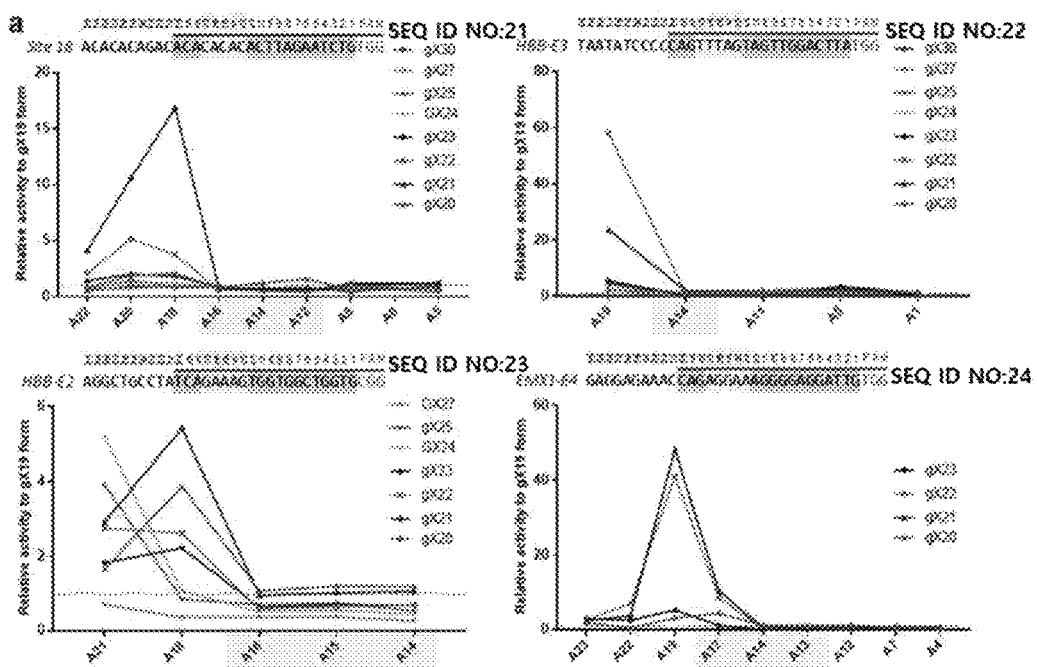
FIG. 4A is a graph showing the relative substitution activity of ABE 7.10 [gX20~30 activity/GX19 activity] at four sites compared to when GX19 sgRNA was used.
Figure 4B:
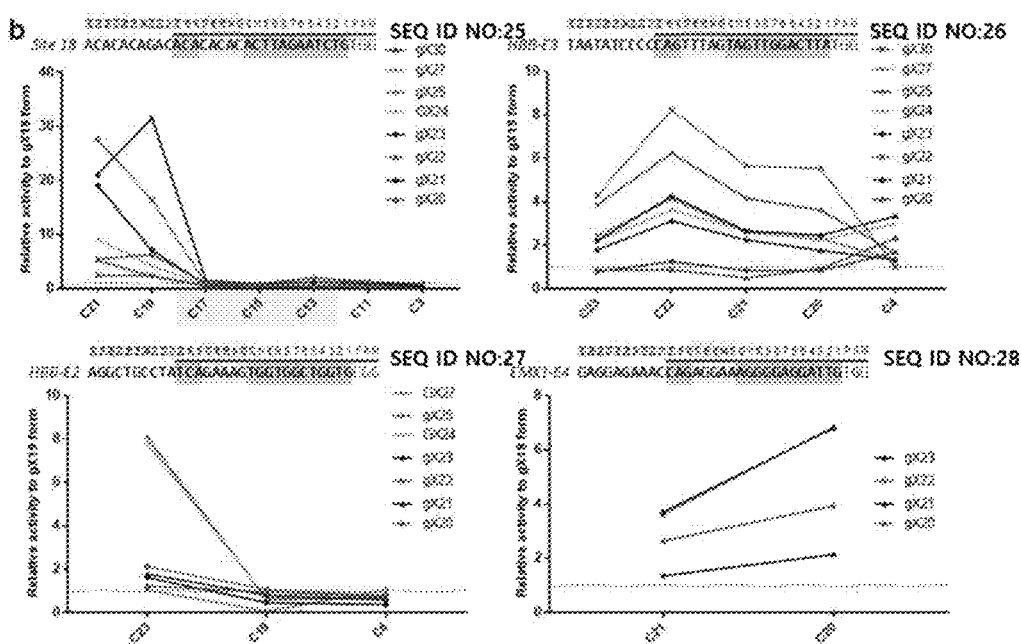
FIG. 4B is a graph showing the relative substitution activity of BE3 [gX20~30 activity/ GX19 activity] compared to when GX19 sgRNA was used, wherein the base-editing window, which is known to operate efficiently when using GX19 sgRNA, is expressed in light blue.

Relative substitution activity of ABE 7.10 [gX20~30 activity/GX19 activity] at four sites was determined compared to when GX19 sgRNA was used, and the results are shown in FIG. 4A. The relative substitution activity of BE3 [gX20~30 activity/GX19 activity] was determined compared to when GX19 sgRNA was used, and the results are shown in FIG. 4B. The base-editing window, which is known to operate efficiently when using GX19 sgRNA, is expressed in light blue. Each activity in the HEK293T cell line was measured by a deep-sequencing method.

Example 4: Test of Change of Base-Editing Window Depending on sgRNA Type in Rapeseed and Soybean The change of the base-editing window depending on the type of sgRNA in rapeseed and soybean, as representatives of eukaryotic plants, was tested and the results are shown in FIGS. 5A to 5D.

Each activity was analyzed through deep sequencing.

When gX19 sgRNA and gX20 sgRNA were used along with the AID2 cytosine base-editor in the rapeseed protoplast, the substitution efficiency depending on the cytosine position was measured, and the results are shown in FIG. 5A.

FIG. 5B shows the change of alleles introduced with mutations occurring most frequently according to the sgRNA type. It was found that a TAG stop codon was produced only when gX20 sgRNA was used.

Figure 5C:
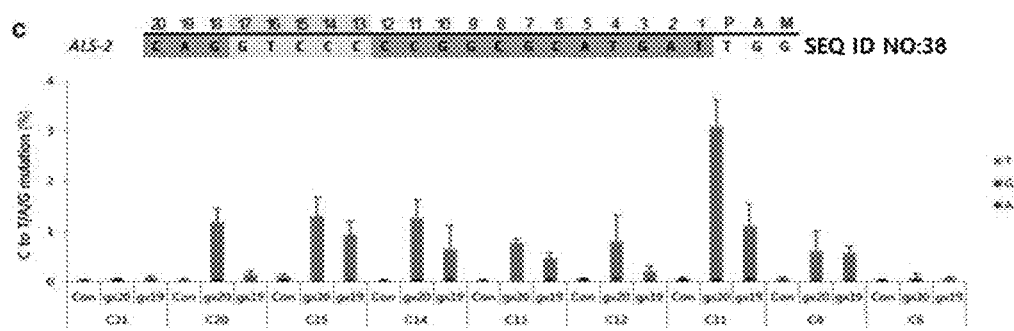
FIG. 5C shows the substitution efficiency depending on the cytosine position when gX19 sgRNA and gX20 sgRNA were used along with the AID2 cytosine base-editor in the soybean protoplast.
Figure 6A:
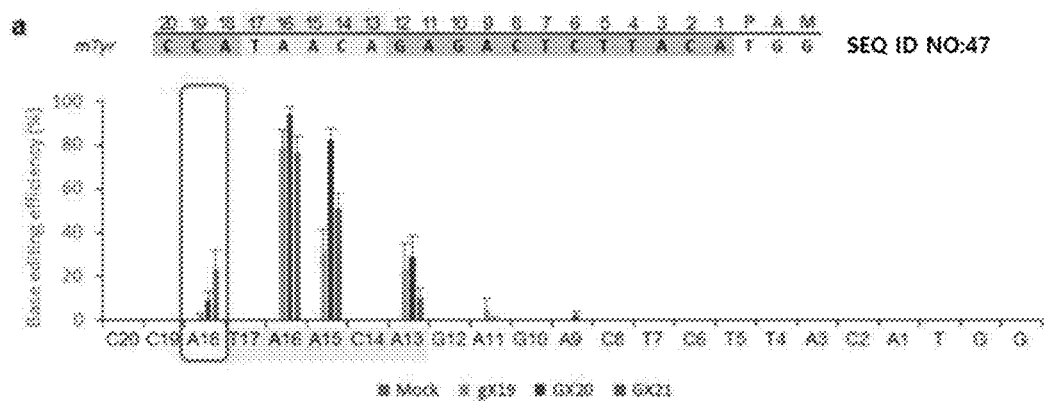
FIG. 6A shows the substitution activity analyzed by deep sequencing in the blastocyst stage after microinjection of ABE 7.10 mRNA along with different types of sgRNA into mouse embryos.

When gX19 sgRNA and gX20 sgRNA were used along with the AID2 cytosine base-editor in the soybean protoplast, the substitution efficiency depending on the cytosine position was measured, and the results are shown in FIG. 5C. The change of alleles introduced with mutations occurring most frequently according to the sgRNA type is shown in FIG. 5D. Similarly, it was found that a TAG stop codon was produced only when gX20 sgRNA was used.

Example 5: Test of Change of Base-Editing Window Depending on sgRNA Type in Mice The change of the base-editing window depending on the type of sgRNA in mice as representatives of eukaryotic animals was tested, and the results are shown in FIGS. 6A and 6B.

After microinjection of ABE 7.10 mRNA with different types of sgRNA into mouse embryos, the substitution activity was analyzed by deep sequencing in the blastocyst stage, and the results are shown in FIG. 6A.

As a result of analyzing pups obtained by performing microinjection into embryos using ABE 7.10 mRNA in combination with GX21 sgRNA, as shown in FIG. 6B, three pups with desired H420R mutations were obtained.

INDUSTRIAL APPLICABILITY

According to the present disclosure, by using a guide RNA extended than a conventional guide RNA for the gene base editing using a deaminase, the frequency and/or efficiency of base editing can be improved, and desired point mutations can be effectively induced using this technology.

Although specific configurations of the present disclosure have been described in detail, those skilled in the art will appreciate that preferred embodiments are given for illustrative purposes in the description and should not be construed as limiting the scope of the present disclosure. Therefore, the substantial scope of the present disclosure is defined by the accompanying claims and equivalents thereto.

SEQUENCE LISTING FREE TEXT

An electronic file is attached.

---

The invention claimed is:

1. A method of producing a genetically modified eukaryotic cell having a base substitution, comprising:
   (a) preparing a composition for base editing comprising
      (i) an adenosine base editor (ABE) or cytosine base editor (CBE),
         wherein the ABE is selected from the group consisting of apolipoprotein B editing complex 1 (APOBEC1) and activation-induced deaminase (AID), the CBE is tRNA-specific adenosine deaminase (tadA);
      (ii) Cas 9 nickase (nCas9); and
      (iii) an extended guide RNA (ggX20) hybridizable with a target sequence,
      wherein the ggX20 comprises a sequence of 20 nucleotides of the target sequence, and two additional non-complementary guanines (G) in front of 20 nucleotides in the 5' direction from protospacer adjacent motif (PAM),
      wherein the target sequence is selected from HEK2, HBB, and FANCF;
   (b) introducing the composition into a eukaryotic cell,
      wherein the extended guide RNA hybridizes with the target sequence,
      wherein the nCas9 makes a single stranded nick,
      wherein the ABE converts an adenosine to a guanine at position 18 of the target sequence in the 5' direction from the PAM;
      wherein the CBE converts a cytosine to a thymine at position 20, 21, or 23 of the target sequence in the 5' direction from the PAM, and
      wherein the base substitution does not cause a double stranded break.

2. The method according to claim 1, wherein the composition further comprises an uracil DNA glycosylase inhibitor (UGI).

3. The method according to claim 1, wherein the composition further comprises a nuclear localization sequence (NLS).

* * * * *

SEQUENCE LISTING

<160> NUMBER OF SEQ ID NOS: 2

<210> SEQ ID NO 1
<211> LENGTH: 60
<212> TYPE: RNA
<213> ORGANISM: Artificial Sequence
<220> FEATURE:
<223> OTHER INFORMATION: guide RNA

<400> SEQUENCE: 1
uagcaaguua aaauaaggcu aguccguuau caacuugaaa aaguggcacc gagucggugc    60

<210> SEQ ID NO 2

```
<211> LENGTH: 21
<212> TYPE: DNA
<213> ORGANISM: Artificial Sequence
<220> FEATURE:
<223> OTHER INFORMATION: NLS sequence

<400> SEQUENCE: 2
cccaagaaga agaggaaagt c                                              21
```